(12) United States Patent  
Lalonde

(10) Patent No.: US 6,602,247 B2  
(45) Date of Patent: Aug. 5, 2003

(54) APPARATUS AND METHOD FOR PERFORMING A TREATMENT ON A SELECTED TISSUE REGION

(75) Inventor: Jean-Pierre Lalonde, Verdun (CA)

(73) Assignee: CryoCath Technologies Inc., Quebec (CA)

( * ) Notice: Subject to any disclaimer, the term of this patent is extended or adjusted under 35 U.S.C. 154(b) by 0 days.

(21) Appl. No.: 10/016,190

(22) Filed: Mar. 12, 2002

(65) Prior Publication Data

US 2002/0099364 A1 Jul. 25, 2002

Related U.S. Application Data

(63) Continuation-in-part of application No. 09/850,668, filed on May 7, 2001, which is a continuation of application No. 09/201,071, filed on Nov. 30, 1998, now Pat. No. 6,235,019, which is a continuation-in-part of application No. 08/893,825, filed on Jul. 11, 1997, now Pat. No. 5,899,899, which is a continuation-in-part of application No. 08/807,382, filed on Feb. 27, 1997, now Pat. No. 5,899,898.

(51) Int. Cl.$^7$ ................................................ A61B 18/18
(52) U.S. Cl. ............................ 606/22; 606/23; 606/21
(58) Field of Search ........................... 606/20–23, 27–28

(56) References Cited

U.S. PATENT DOCUMENTS

| | | | | |
|---|---|---|---|---|
| 3,125,096 A | * | 3/1964 | Antiles et al. ............... 607/105 |
| 3,910,277 A | | 10/1975 | Zimmer .................... 128/303.1 |
| 4,375,220 A | | 3/1983 | Matvias ....................... 128/804 |
| 4,660,571 A | | 4/1987 | Hess et al. ................... 128/784 |
| 4,664,120 A | | 5/1987 | Hess ........................... 128/642 |
| 4,690,155 A | | 9/1987 | Hess ........................... 128/786 |
| 4,699,147 A | | 10/1987 | Chilson et al. .............. 128/642 |
| 4,709,698 A | | 12/1987 | Johnston et al. ......... 128/303.12 |
| 4,754,752 A | | 7/1988 | Ginsburg et al. ....... 128/303.12 |
| 4,776,349 A | | 10/1988 | Nashef et al. .............. 128/786 |
| 4,945,912 A | | 8/1990 | Langberg .................... 128/642 |
| 4,946,440 A | | 8/1990 | Hall ............................. 604/95 |
| 4,979,948 A | | 12/1990 | Geddes et al. ................. 606/33 |
| 4,998,916 A | | 3/1991 | Hammerslag et al. ......... 604/95 |
| 4,998,933 A | | 3/1991 | Eggers et al. .................. 606/41 |
| 5,007,437 A | | 4/1991 | Sterzer ......................... 428/786 |
| 5,010,894 A | | 4/1991 | Edhag .......................... 128/785 |
| 5,078,713 A | | 1/1992 | Varney ......................... 606/23 |
| 5,100,388 A | | 3/1992 | Behl et al. ................... 604/113 |
| 5,139,496 A | | 8/1992 | Hed .............................. 606/23 |
| 5,147,355 A | | 9/1992 | Friedman et al. ............. 606/23 |
| 5,224,943 A | | 7/1993 | Goddard ....................... 606/20 |
| 5,228,442 A | | 7/1993 | Imran .......................... 128/642 |
| 5,231,995 A | | 8/1993 | Desai .......................... 128/784 |
| 5,281,213 A | | 1/1994 | Milder et al. ................. 606/15 |
| 5,281,215 A | | 1/1994 | Milder .......................... 606/20 |
| 5,293,869 A | | 3/1994 | Edwards et al. ............. 128/642 |
| 5,324,286 A | | 6/1994 | Fowle .......................... 606/23 |
| 5,334,181 A | | 8/1994 | Rubinsky et al. ............. 606/22 |
| 5,342,295 A | | 8/1994 | Imran ........................... 604/43 |
| 5,403,309 A | | 4/1995 | Coleman et al. .............. 606/20 |
| 5,423,807 A | | 6/1995 | Milder .......................... 606/20 |
| 5,452,582 A | | 9/1995 | Longsworth ................. 62/51.2 |
| 5,487,385 A | | 1/1996 | Avitall ........................ 128/642 |
| 5,517,989 A | | 5/1996 | Frisbie et al. ............... 128/642 |
| 5,520,682 A | | 5/1996 | Baust et al. .................. 606/24 |
| 5,545,200 A | | 8/1996 | West et al. .................. 607/122 |
| 5,624,392 A | * | 4/1997 | Saab ............................. 604/43 |
| 5,792,105 A | | 8/1998 | Lin et al. ...................... 604/96 |
| 5,800,482 A | | 9/1998 | Pomeranz et al. .......... 607/101 |
| 5,810,802 A | | 9/1998 | Panescu et al. ............... 606/31 |

OTHER PUBLICATIONS

WO 91/05528, Van Liebergen, Device for Cooling or Heating a Person, May 2, 1991.*

* cited by examiner

*Primary Examiner*—Roy D. Gibson  
(74) *Attorney, Agent, or Firm*—Christopher & Weisberg, P.A.

(57) ABSTRACT

A cryogenic catheter includes an outer flexible member having at least one cryogenic fluid path through the flexible member. The at least one fluid path is defined by a plurality of flexible members disposed within the outer flexible member.

33 Claims, 14 Drawing Sheets

|  | PRESS. [psi] | TEMPERATURE [°C] | | | |
|---|---|---|---|---|---|
|  |  | TIP | RING1 | RING2 | RING3 |
| Test I |  |  |  |  |  |
|  | 230 | -45 | 6 | 16 | 13 |
|  | 250 | -45 | -36 | 3 | 1 |
|  | 270 | -43 | -43 | -19 | -20 |
|  | 290 | -40 | -47 | -23 | -22 |
|  | 310 | -40 | -47 | -32 | -25 |
|  | 330 | -39 | -47 | -38 | -27 |
|  | 350 | -39 | -47 | -47 | -31 |
|  | 370 | -40 | -47 | -48 | -45 |
|  | 390 | -39 | -47 | -48 | -49 |
|  | 410 | -36 | -46 | -47 | -49 |
|  | 430 | -36 | -46 | -48 | -49 |
| Test II |  |  |  |  |  |
|  | 235 | -50 |  |  |  |
|  | 275 | -51 | -52 | -4 | 6 |
|  | 300 | -44 | -50 | -53 | -2 |
|  | 325 | -43 | -51 | -52 | -24 |
|  | 350 | -43 | -50 | -51 | -33 |
|  | 375 | -42 | -49 | -50 | -52 |
|  | 400 | -40 | -49 | -50 | -53 |
|  | 425 | -39 | -48 | -49 | -51 |
|  | 449 | -37 | -47 | -48 | -50 |
| Test III |  |  |  |  |  |
|  | 235 | -48 | -40 | 20 | 25 |
|  | 275 | -48 | -42 | 0 | 5 |
|  | 300 | -47 | -47 | -38 | -8 |
|  | 325 | -45 | -49 | -44 | -25 |
|  | 350 | -42 | -51 | -51 | -35 |
|  | 375 | -41 | -49 | -52 | -51 |
|  | 400 | -38 | -47 | -48 | -52 |
|  | 425 | -38 | -47 | -48 | -53 |
|  | 449 | -36 | -47 | -47 | -50 |

FIG. 19

APPARATUS AND METHOD FOR PERFORMING A TREATMENT ON A SELECTED TISSUE REGION

CROSS-REFERENCE TO RELATED APPLICATIONS

This application is a continuation-in-part of U.S. patent application Ser. No. 09/850,668 filed May 7, 2001, entitled "Cryosurgical Catheter," which is a continuation of U.S. patent application Ser. No. 09/201,071 filed Nov. 30, 1999, U.S. Pat. No. 6,235,019, entitled "Cryosurgical Catheter," which is a continuation-in-part of U.S. patent application Ser. No. 08/893,825 filed Aug. 11, 1997, U.S. Pat. No. 5,899,899 entitled "Cryosurgical Linear Ablation Structure," which is a continuation-in-part of U.S. patent application Ser. Nos. 08/807,382 file Feb. 27, 1997, U.S. Pat. No. 5,899,898, entitled "Cryosurgical Linear Ablation."

STATEMENT REGARDING FEDERALLY SPONSORED RESEARCH

Not Applicable

FIELD OF THE INVENTION

The invention relates to catheters, and more particularly to cryosurgical catheters used for tissue ablation.

BACKGROUND OF THE INVENTION

Many medical procedures are performed using minimally invasive surgical techniques, wherein one or more slender implements are inserted through one or more small incisions into a patient's body. With respect to ablation, the surgical implement can include a rigid or flexible structure having an ablation device at or near its distal end that is placed adjacent to the tissue to be ablated. Radio frequency energy, microwave energy, laser energy, extreme heat, and extreme cold can be provided by the ablation device to kill the tissue.

With respect to cardiac procedures, a cardiac arrhythmia can be treated through selective ablation of cardiac tissue to eliminate the source of the arrhythmia. A popular minimally invasive procedure, radio frequency (RF) catheter ablation, includes a preliminary step of conventional electrocardiographic mapping followed by the creation of one or more ablated regions (lesions) in the cardiac tissue using RF energy. Multiple lesions are frequently required because the effectiveness of each of the proposed lesion sites cannot be predetermined due to limitations of conventional electrocardiographic mapping. Often, five lesions, and sometimes as many as twenty lesions may be required before a successful result is attained. Usually only one of the lesions is actually effective; the other lesions result in unnecessarily destroyed cardiac tissue.

Deficiencies of radio frequency ablation devices and techniques have been overcome by using cold to do zero degree or ice mapping prior to creating lesions, as taught in U.S. Pat. Nos. 5,423,807; and 5,281,213; and 5,281,215. However, even though combined cryogenic mapping and ablation devices permit greater certainty and less tissue damage than RF devices and techniques, both the cryogenic and the RF devices are configured for spot or roughly circular tissue ablation.

Spot tissue ablation is acceptable for certain procedures. However, other procedures can be more therapeutically effective if multiple spot lesions along a predetermined line, or a single elongate or linear lesion is created in a single ablative step. Radio frequency ablation devices are known to be able to create linear lesions by dragging the ablation tip along a line while it is active. However, no cryogenic devices are known that are optimized for, or which are even minimally capable of, creating an elongate lesion.

SUMMARY OF THE INVENTION

According to one aspect, the present invention provides a medical device having a body which includes a fluid transport member disposed within the body. An outer member substantially surrounds the fluid transport member. A chamber is formed between the outer member and the fluid transport member. A means to vary the relative distance between the outer membrane and the fluid transport member is included.

As another aspect, the present invention provides a medical device which has a thermally transmissive region, and an axially off-set fluid path thermally coupled to at least a portion of the thermally transmissive region. The axially off-set fluid path is adjacent to an inner surface of the thermally transmissive region.

yet another aspect, the present invention provides a medical device having a body which includes a thermally transmissive region disposed on the surface of the body and a rotatable fluid transport member thermally coupled to the thermally transmissive region. The rotatable fluid transport member has at least one segment that is proximally positionable to an inner surface of the thermally transmissive region.

According to a further aspect, the present invention provides a medical device having a body which includes a thermally transmissive region disposed on the surface of the body, a support slide disposed within the body and proximal to the thermally transmissive region, and a flexible fluid transport member slidably mounted to the support slide.

According to yet another aspect, the present invention provides a method of treating a selected portion of tissue. An appropriate medical device having a fluid transport path and a thermally transmissive region disposed therein is provided. The medical device is located within the selected portion of tissue. A flexible member which substantially surrounds the thermally transmissive region is inflated. The fluid transport path is moved to a selected portion of the flexible member. A thermally active fluid is circulated within the fluid transport path to deliver a medically effective amount of thermal energy to the selected portion of tissue.

According to still yet another aspect, the present invention provides a method of delivering a medically efficacious amount of energy to a selected tissue using a medical device having a thermally transmissive region, an expandable membrane substantially surrounding the thermally transmissive region and a thermal fluid path thermally coupled to the thermally transmissive region. At least a portion of the thermally transmissive region is positioned adjacent to the selected tissue. The selected tissue is compressed by activating the expandable membrane. The thermal fluid path is moved to a position proximal to an inner surface of the expandable membrane. A thermally active fluid is circulated within the thermal fluid path which transfers a therapeutic amount of energy to the selected tissue.

In yet another aspect, the present invention provides a method of treating a tissue using a medical device which has a thermally transmissive region and an axially off-center fluid path thermally coupled to the thermally transmissive region. At least a portion of the thermally transmissive region is positioned proximal to the tissue to be treated. The axially off-center fluid path is positioned closest to the portion of the thermally transmissive region which is proximal to the tissue to be treated. An energetic fluid is circulated within the axially off-center fluid path.

According to still another aspect, the present invention provides a method of treating a selected tissue which uses a medical device that has a thermally transmissive region, an expandable member substantially surrounding the thermally transmissive region and a moveable fluid path thermally coupled to the thermally transmissive region. The expandable member is expanded against the selected tissue. The moveable fluid path is moved in a direction towards the selected tissue. An energetic fluid is circulated within the moveable fluid path to deliver a medically effective amount of thermal energy to the selected tissue.

In yet a further aspect, the present invention provides a method of treating a selected tissue which utilizes a medical device with a body, a fluid transport member disposed within the body, an outer member substantially surrounding the fluid transport member, a chamber disposed between the outer member and the fluid transport member; and a means to vary a relative distance between the outer member and the fluid transport member. The medical device is positioned to contact the selected tissue. The outer member is expanded by injecting a bio-compatible fluid into the chamber. The relative distance between the fluid transport member and the outer member is decreased until a selected distance is reached. A thermally active fluid is injected into the fluid transport member for a medically effective period of time.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 19 is a table illustrating cooling performance of a catheter in accordance with the invention;

DETAILED DESCRIPTION OF THE INVENTION

Figure 1:
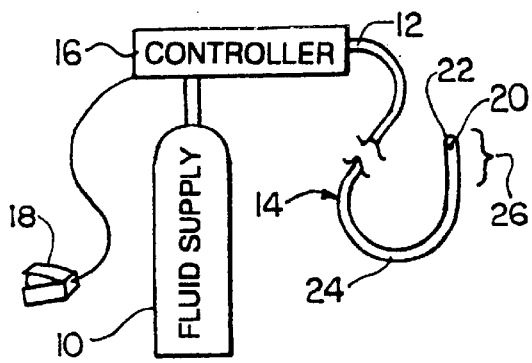
FIG. 1 is a schematic illustration of an embodiment of a cryosurgical system in accordance with the invention.

FIG. 1 is a schematic illustration of a cryosurgical system in accordance with the invention. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example a temperature sensor can be placed at a point proximate the distal end 22 of the catheter and other temperature sensors 20 can be placed at spaced intervals between the distal end of the catheter and another point that is between the distal end and the proximal end.

The cryogenic fluid can be in a liquid or a gas state. An extremely low temperature can be achieved within the catheter, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50—50 mixture of difluoromethane & pentafluoroethane sold by Allied Signal), and CFC's such as Dupont's Freon. Exemplary gasses include nitrous oxide, and carbon dioxide.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Although described in greater detail below, exemplary fluid paths can be one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat.

For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures.

Furthermore, while the thermally-transmissive region 26 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue. Additional details of the thermally-transmissive region 26 and the thermal transfer process are described in greater detail below.

In exemplary embodiments of the invention, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a cord, wire or cable can be incorporated with, or inserted into, the catheter for deformation of the thermally transmissive region 26.

Figure 2:
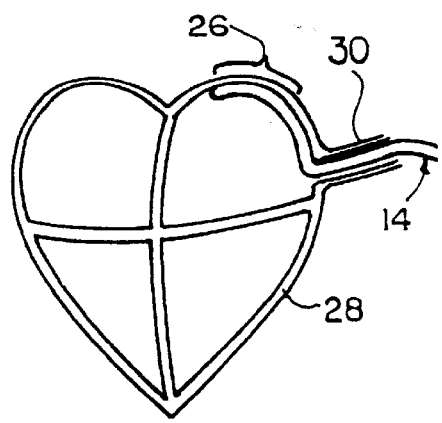
FIG. 2 is a schematic depiction of the chambers of the heart showing placement of the catheter of FIG. 1.

The cryogenic system of FIG. 1 is better understood with reference to its use in an operative procedure as shown in FIG. 2. Following the determination of a proposed lesion site within a heart chamber 28, for example, the catheter 14 is directed through a blood vessel 30 to a region within the heart, such as an atrial or ventricular chamber, where the lesion will be made. The thermally-transmissive region 26 is placed proximate to the tissue to be ablated. The thermally-transmissive region of the catheter may be deformed to conform to the curvature of the tissue before, during, or after placement against the tissue. The controller 16 allows or causes cryogenic fluid to flow from the cryogenic fluid supply 10 to the fluid path in the catheter 14 and thence to the thermally-transmissive region 26 to ablate the desired area or to cold map along the same tissue area. In one embodiment (e.g., FIG. 12) a first conduit is concentric within a second conduit and cooling fluid travels to a thermally-transmissive region proximate a closed distal end of the catheter through a first conduit (fluid path) and is exhausted from the catheter through the second conduit (fluid path).

Having described the function of the cryogenic catheter 14 and its use in a system context, several exemplary embodiments of the thermally-transmissive region 26 of the catheter are now described in greater detail. FIGS. 3, 4, 5, 12–16 and 18 illustrate embodiments of the catheter, or portions thereof, having two or more thermally-transmissive segments in a spaced-apart relationship. Each of the illustrated catheters includes a closed tip 32 that can include a thermally-transmissive material.

Figure 3:
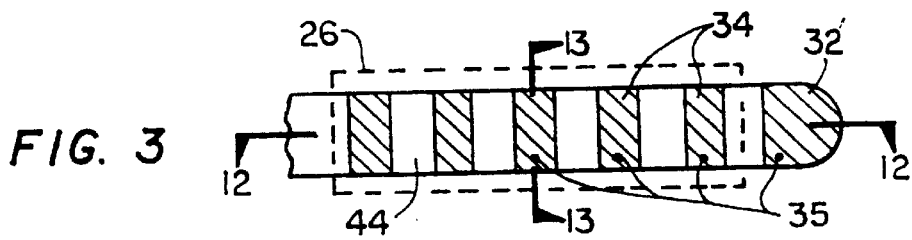
FIG. 3 illustrates the tip region of one embodiment of the catheter in accordance with the invention.
Figure 13:
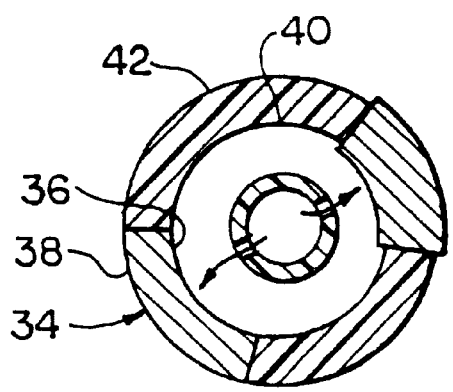
FIG. 13 is a sectional view of the catheter of FIG. 3 taken along line 13—13.
Figure 14:
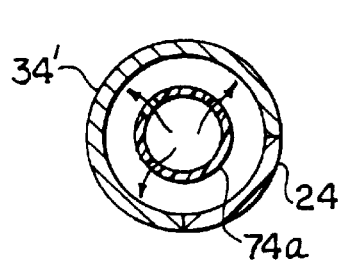
FIGS. 14–16 are sectional views of additional catheter embodiments.
Figure 15:
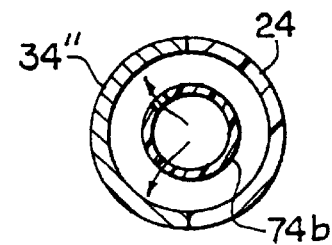
Figure 16:
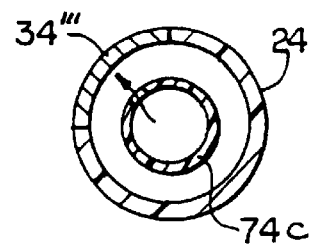

Referring specifically to the embodiment depicted in FIG. 3, multiple thermally-transmissive elements 34 are integral with a distal portion of a catheter. Each of the thermally-transmissive elements 34 includes a first side or face 36 (shown in FIGS. 12 and 13) exposed to a cryogenic fluid path and cryogenic fluid (shown by arrows) and a second side or face 38 exposed to points exterior to the catheter. As shown in FIG. 13, the first side 36 and/or second side 38 of any or all of the thermally-transmissive elements 34 can be substantially flush with, recessed below, or protruding from the inner surface 40 and outer surface 42 of a portion of the catheter. The thermally-transmissive elements 34 are separated by flexible portions of material 44 than can range from slightly less thermally-transmissive than the adjacent thermally-transmissive elements to substantially less thermally-transmissive than the adjacent elements. In the illustrated embodiment of FIG. 3, the thermally-transmissive elements 34 are annular, cylindrical elements which are made of gold-plated copper or bronze. Thermocouples 35 can be associated with one or more of the elements 34 and the tip 32. The thermally-transmissive elements 34 can be completely exposed, embedded, or a combination thereof along the full 360° of the catheter's circumference. In certain applications the thermally-transmissive elements traverse or define less than 360 ° of the catheter's circumference as shown in FIGS. 14–16 and as described below. The longitudinal width of each thermally-transmissive element 34, the spacing between elements, the material thickness, and the material composition are matched with a selected cryogenic fluid, one or more cryogenic fluid delivery locations within the catheter and fluid delivery pressure to produce overlapping cold regions which produce a linear lesion.

Figure 4:
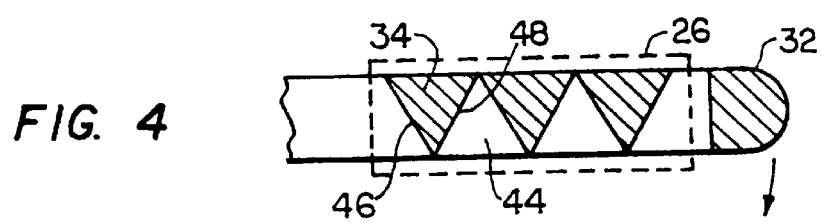
FIG. 4 illustrates an alternative embodiment of the catheter of FIG. 3.

The embodiment illustrated in FIG. 4 is substantially identical to the embodiment of FIG. 3, however, at least one of the thermally-transmissive elements 34 includes a first open end 46 that defines a first plane and a second open end 48 that defines a second plane, wherein the first and second planes intersect to give the annular elements a wedge-like appearance. Such a configuration permits adjacent thermally-transmissive elements 34 to be positioned very closely together, but it can limit the possibilities for deforming the thermally-transmissive region 26, which, in this embodiment, is flexible in the direction indicated by the arrow.

Figure 5:
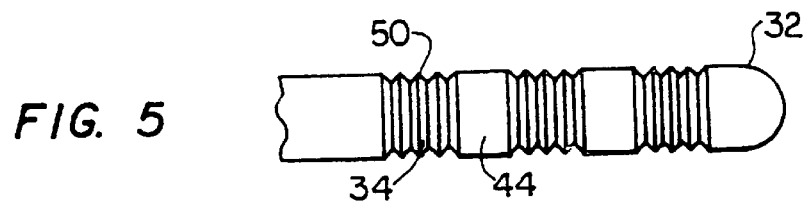
FIG. 5 illustrates yet another embodiment of the catheter.

With respect to the embodiments shown in both FIGS. 3 and 4, the thermally-transmissive elements 34 are substantially rigid and are separated and/or joined by a flexible material 44. However, in other embodiments the thermally-transmissive elements 34 are flexible and are interdigitated with either rigid or flexible segments. FIG. 5, for example, illustrates an embodiment of the cryogenic catheter having three thermally-transmissive elements 34 that are flexible. The flexibility is provided by a folded or bellows-like structure 50. In addition to being shapable, a metal bellows can have enough stiffness to retain a selected shape after a deforming or bending step.

Figure 6:
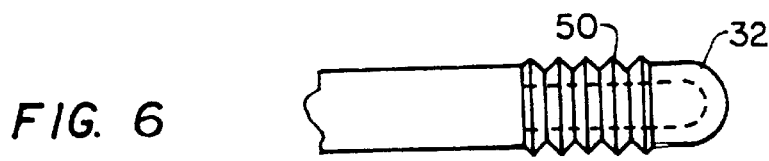
FIG. 6 illustrates a deformable tip for a catheter.

Instead of, or in addition to, flexible, thermally-transmissive elements 34 and/or flexible material 44 between elements, the distal tip 32 (or a portion thereof) can be deformable. For example, FIG. 6 illustrates a tip 32 having thermally-transmissive, flexible, bellows 50.

Figure 7:
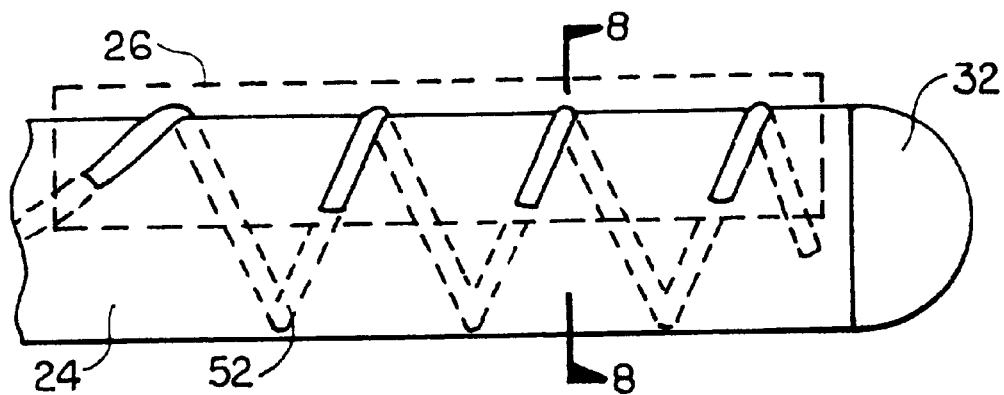
FIG. 7 illustrates yet another embodiment of the catheter.
Figure 8:
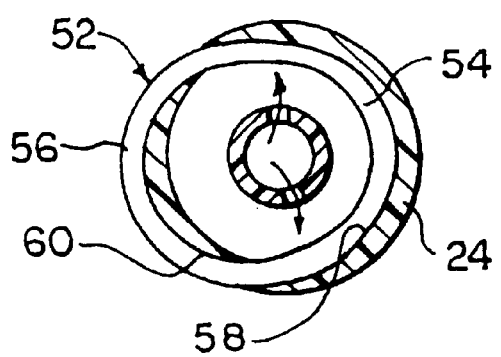
FIG. 8 is a sectional view of the catheter of FIG. 7 taken along line 8—8.

Referring now to FIGS. 7–10, a different approach is shown for providing multiple thermally-transmissive segments in a spaced-apart relationship. FIG. 7 illustrates a catheter embodiment having an elongate, thermally-transmissive region 26 that includes a helical coil 52 at least partially embedded in the flexible member 24. As shown in FIG. 8, at least a first portion 54 of the helical coil 52 is exposed to a fluid path within the flexible member 24 and a second portion 56 of the helical coil is exposed to the exterior of the flexible member. As described above with respect to FIG. 13, the first portion 54 of the coil can be substantially flush with, recessed below, or protruding from an inner surface 58 of the flexible member 24. Similarly, the second portion 56 of the coil 52 can be substantially flush with, recessed below, or protruding from an outer surface 60 of the flexible member 24.

In the embodiment of FIG. 8, the second portion 56 of the coil 52 is exposed along only a portion of the outer circumference of the flexible member 24 to define a longitudinally-elongate, thermally-transmissive region 26. This configuration can be provided by eccentrically mating the helical coil 52 to the catheter so that the longitudinal axis of the coil and the longitudinal axis of the catheter are substantially parallel. The eccentric positioning of the coil 52 provides excellent cooling performance because the surface area available for thermal exchange between the first portion 54 of coil and the cryogenic fluid is greater than the surface area available for thermal exchange between the second portion 56 of the coil and adjacent tissue where cooling power is delivered by each exposed coil portion to provide a linear lesion.

Figure 9:
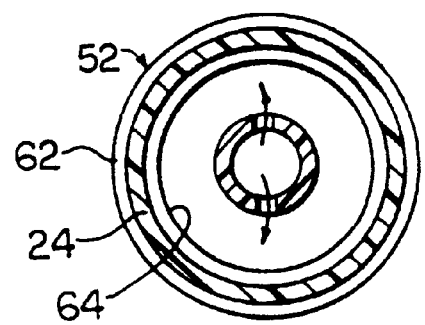
FIG. 9 a sectional view of an alternative embodiment of the linear ablation catheter illustrated in FIG. 7.

Referring now to FIG. 9, an alternative embodiment is shown wherein a first portion 62 of the coil 52 is exposed around the entire circumference of the flexible member 24, and a second portion 64 is exposed to a fluid path around the inner surface of the flexible member 24. This is achieved by having the longitudinal axis of the helical coil 52 co-axial with the longitudinal axis of the catheter.

Figure 10:
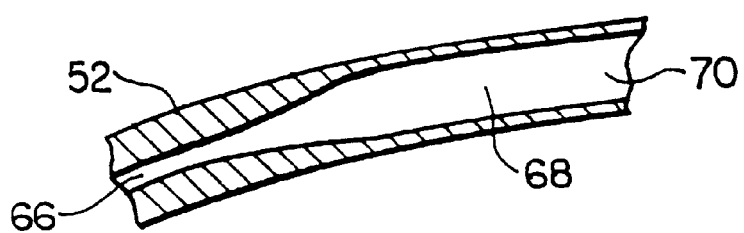
FIG. 10 illustrates an expansion chamber within a portion of a helical coil.

In the embodiments illustrated in FIGS. 7–9, the coil 52 is solid. However, in other embodiments the coil can be an elongate, hollow, gas expansion chamber. For example, FIG. 10 illustrates a portion of a helical coil 52 that includes a passage that defines at least a portion of a fluid path through a flexible member of the catheter. The coil 52 defines a first fluid path diameter at a fluid entry point 66 and a second fluid path diameter that is greater than the first fluid path diameter at a gas expansion or boiling location 68. Gas escaping from a fluid exit point 70 can be exhausted through an open central region of the coil and/or another passage through the flexible member 24.

Figure 11:
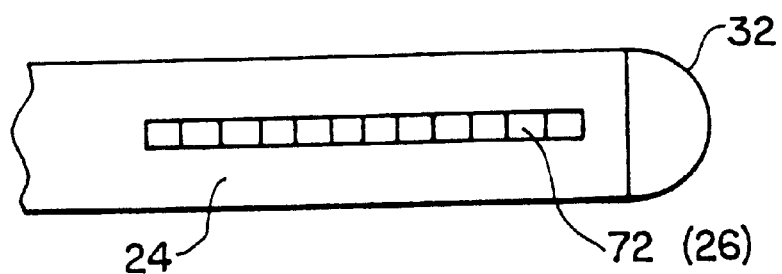
FIG. 11 illustrates a portion of a catheter having an elongate, thermally-transmissive strip.

FIG. 11 illustrates an embodiment of the catheter wherein a continuous, elongate, thermally-transmissive strip 72 is longitudinally integrated with a flexible member 24. The strip can include a bellows-like structure. As described above with respect to other embodiments, a first portion of the strip can be substantially flush with, recessed below, or protrude from the outer surface of the flexible member. Similarly, a second portion of the strip can be substantially flush with, recessed below, or protrude from an inner surface of the flexible member.

Figure 12:
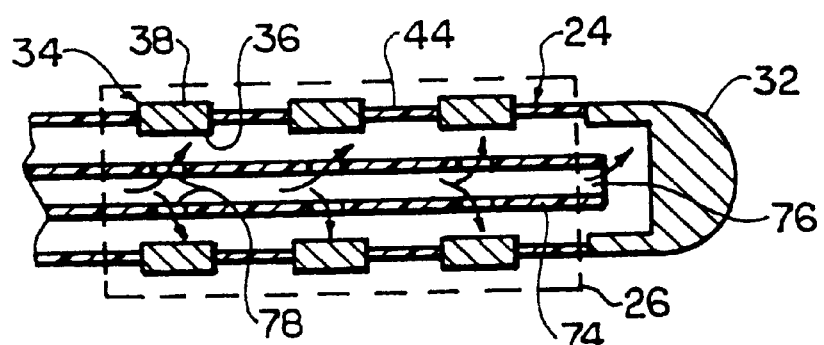
FIG. 12 is a sectional view of the catheter of FIG. 3 taken along line 12—12.

Referring now to FIG. 12, an embodiment of the catheter is illustrated having a second or inner flexible member 74 within a lumen of first or outer flexible member 24, wherein the second flexible member defines a fluid path to the thermally-transmissive region 26. The inner member 74 can include a single opening 76 at or near the tip 32. Cryogenic fluid is expelled from the opening 76 and returns to the proximal end of the catheter along a fluid path defined by the outer wall of the inner member 74 and the inner wall of the outer member 24. This fluid path configuration is also partially illustrated in FIGS. 8, 9, and 13. Alternatively, as also shown in FIG. 12, the inner member 74 can be provided with multiple openings 78 proximate to and/or aligned with the inner face of one or more thermally-transmissive elements 34 to achieve more uniform cooling across the entire elongate, thermally-transmissive region 26.

Referring now to FIGS. 14–16, sectional views of catheter embodiments are illustrated to show alternative configurations for thermally-transmissive elements. The previously described thermally-transmissive elements 34 are arcuate and form complete and continuous 360 degree structures that traverse the complete circumference of the catheter, notwithstanding being flush with, depressed below, or raised above the outermost surface of the flexible member 24. However, the arcuate elements 34', 34", and 34'" illustrated in FIGS. 14–16, respectively, traverse less than 360 degrees of the circumference of the first flexible member and do not form complete loops. For example, in FIG. 14, element 34' defines an approximately 270 degree arc. In FIG. 15 the thermally-transmissive element 34" defines an approximately 180 degree arc; and in FIG. 16, the thermally-transmissive element 34'" defines an approximately 90 degree arc. A catheter can include combinations of element types, such as a complete ring or loop element, a 270 degree element and a 180 degree element as desired to define a thermally transmissive region. In addition to the having applicability with respect to rigid thermally-transmissive elements, the bellows-like elements can also be less than 360 degrees.

The less than 360 degree arcuate elements provide unique functional benefits with respect to thermal transfer and flexibility of the thermally-transmissive region. For example, because the portion of the catheter between the opposing ends of element 34', 34", 34'" does not include a rigid structure, but rather only the resilient material of flexible member 24, the thermally-transmissive region of the catheter can be more tightly curved (gap between ends inward and element facing outward) than it could with complete 360 degree structures, especially if the elements are relatively long longitudinally.

The inner member 74 can be adapted to direct cooling fluid at only the thermally transmissive element(s) and the shape and/or the number of openings for cooling fluid can be configured differently depending on the length of the arc defined by the thermally-transmissive element(s). For example, FIG. 14 illustrates an embodiment of the inner member having three openings opposing the thermally transmissive element 34'; FIG. 15 illustrates two openings for a smaller arc; and FIG. 16 discloses a single opening for an even smaller arc.

Another advantage to providing one or more thermally-transmissive elements that have a less than 360 degree configuration is that limiting the span of the elements to a desired lesion width, or somewhat greater than a desired lesion width, reduces the thermal load on the system and/or permits colder temperatures to be achieved than with respect to a complete 360 degree structure. Unnecessary and perhaps undesirable cooling does not occur at any other location along the catheter except at an elongate region of predetermined width. A similar effect can also be achieved by providing a non-circular 360 degree element or by eccentrically mounting a circular 360 degree element with respect to the flexible member, wherein a portion of the 360 degree element is embedded within the wall of the flexible member or otherwise insulated from the cryogenic fluid path in a manner similar to that shown in FIG. 8.

Figure 17:
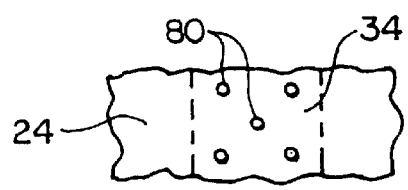
FIG. 17 illustrates an inner face of a flexible catheter member.

Referring now to FIG. 17, a portion of the inner face of an outer flexible member showing in an exemplary embodiment, thermal transfer pins 80 protruding from the inner face of a thermally-transmissive element 34. The pins permit thermal transfer through the flexible member 24. As with the other features of the invention, the pins are equally suitable for complete 360 degree element structures or less than 360 degree structures. Although only pins are shown on any geometric or surface means to increase heat transfer including but not limited to pins, irregularities, channels or surface modifications may be used.

Figure 18:
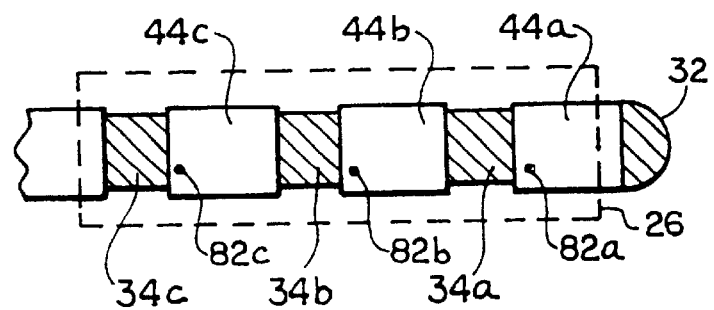
FIG. 18 depicts yet another embodiment of a catheter in accordance with the invention.

Referring now to FIG. 18, yet another embodiment of the catheter is shown wherein rigid metal rings 34a–c are interdigitated with flexible segments 44a–c to define a first flexible member and a thermally-transmissive region approximately one inch in length. A second flexible member is concentric within the first flexible member and has an outlet for cryogenic fluid at its distal end. Thermocouples 82a–c can be associated with one or more of the rings 34a–c.

It has been described above how the thermal loading of a cooling system can be reduced by providing thermally-transmissive elements that span less than 360 degrees. However, the thermal loading can also be reduced by sequentially cooling the thermally-transmissive region. One way to sequentially cool is to modulate the pressure of the cooling fluid along the fluid path through the flexible member. This modulation can be performed by the fluid controller which can be programmed to increase and decrease the pressure of the fluid by predetermined pressure increments over predetermined time intervals. When the cryogenic fluid is a liquid that provides cooling by changing phase from liquid to gas, the change of pressure alters the physical location along the fluid path where the phase change takes place and concomitantly changes the point of coldest temperature along the thermally-transmissive region. Thus, varying the pressure of the fluid can provide a moving ice-formation "front" along the catheter, enabling the creation of a linear lesion.

Therefore, a method of forming an elongate tissue lesion can include the following steps using any of the above described catheters having an elongate, thermally-transmissive region. In a first step a cryogenic fluid is introduced into the flexible member at a first predetermined pressure. Next, the pressure of the cryogenic fluid is incrementally increased within the flexible member until a second predetermined pressure is achieved. Similarly, the pressure of the cryogenic fluid within the flexible member can be decreased incrementally from the second predetermined pressure to the first predetermined pressure, wherein the steps of incrementally increasing and decreasing the pressure define a thermal cycle. Typically, from one to eight thermal cycles are required to achieve a desired therapeutic effect. In an exemplary method, about ten increments of about five seconds in duration are selected and pressure is increased by about 20 to 40 pounds per square inch in each increment. Thus, using this method an elongate lesion can be created in less than 20 minutes.

FIG. 19 is a table that illustrates sequential cooling in a catheter as described above having a thermally-transmissive region that includes a tip and three elements or rings. The table illustrates three tests conducted in a still bath at 37° C., using AZ-20 as the cryogenic fluid. Associated with each pressure increment are measured temperatures at the tip, first ring, second ring, and third ring. The shaded region illustrates the sequential movement of a target temperature range (upper –40's to low –50's) in response to a change in pressure. Although values are only provided for three rings, a similar effect and pattern is obtained with more than three rings or elements.

Figure 20:
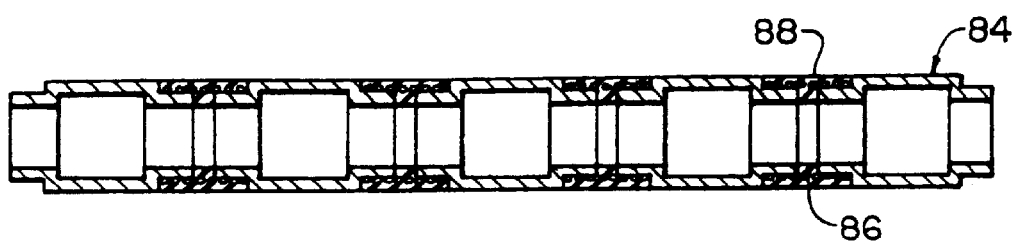
FIG. 20 is a sectional view of another catheter embodiment.

Turning now to FIG. 20, a thermally-transmissive portion of another embodiment of a medical device or structure such as a catheter is illustrated in a sectional view. The structure can include an inner passage or lumen as described above with respect to other embodiments, but which is not shown in this illustration for purposes of clarity. Thus, the illustrated portion is the outer passage or lumen that defines an elongate ablation region. Thermally-transmissive elements 84, such as gold plated copper, are joined to adjacent elements by resilient connecting elements 86, such as a stainless steel springs welded to the ends of the elements 84. A resilient bio-compatible material 88 covers the connecting elements 86 and the interstices between adjacent thermally-transmissive elements. In an exemplary embodiment, the material 88 is vulcanized silicone. It should be noted in the illustration that the surface of the elements 84 is contiguous and co-planar with the material 88 to provide a smooth outer surface.

Figures 21, 22:
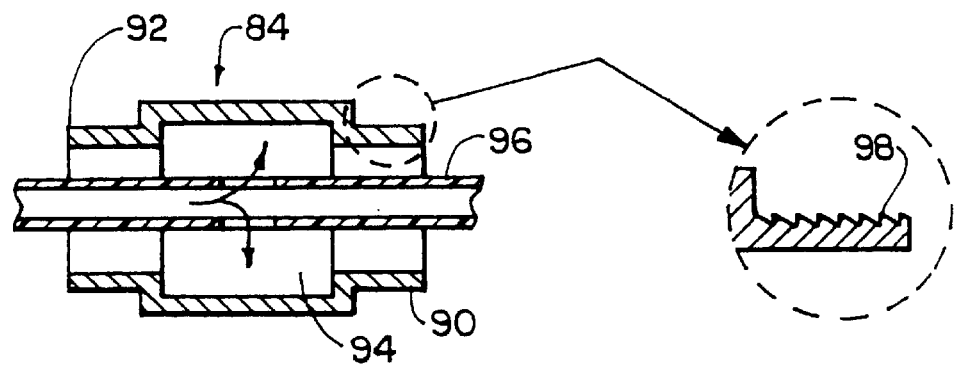
FIG. 21 is a sectional view of a portion of the catheter of FIG. 20.
FIG. 22 is a detailed view of an area of the catheter portion illustrated in FIG. 21.

FIG. 21 illustrates a single thermally-transmissive element 84 having reduced diameter ends 90 and 92. The wider central portion 94 provides an expansion chamber for gas (shown by arrows) exiting an apertured inner passage 96. FIG. 22 shows additional detail of the end 90 of the element 84. The end 90 is textured, such as by providing serrations 98, to provide a good adhesion surface for the material 88.

Figure 23:
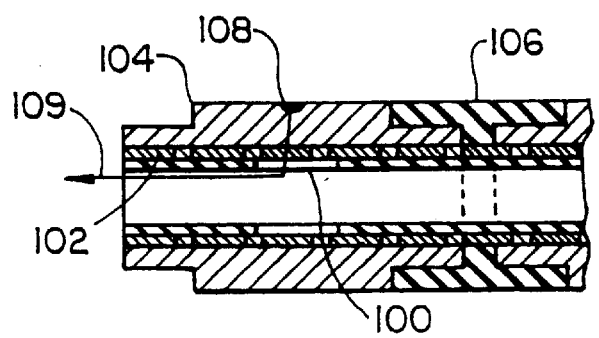
FIG. 23 is an illustration of yet another catheter embodiment.

Referring now to FIG. 23, a thermally-transmissive portion of yet another embodiment of a flexible cryogenic structure is illustrated in a sectional view. In this embodiment an inner, apertured structure 100 has a flat wire 102 wrapped around it in a spiral manner. Thermally-transmissive segments 104 are disposed upon the wire 102 in a spaced-apart relationship, and a flexible, bio-compatible material 106 fills the interstices between segments 104. A thermocouple 108 can be associated with each segment 104. A wire 109 connects the thermocouple 108 to instrumentation near the proximal end of the structure. The exterior surface of the structure is smooth, and the structure can include 3 to 12 segments 104. In an exemplary embodiment the inner structure 100 is made of PTFE, the material 106 is 33 D Pebax, and the wire 102 is stainless steel or Nitinol. An apertured inner passage (similar to that shown in FIG. 21) is placed within the structure.

Figure 24:
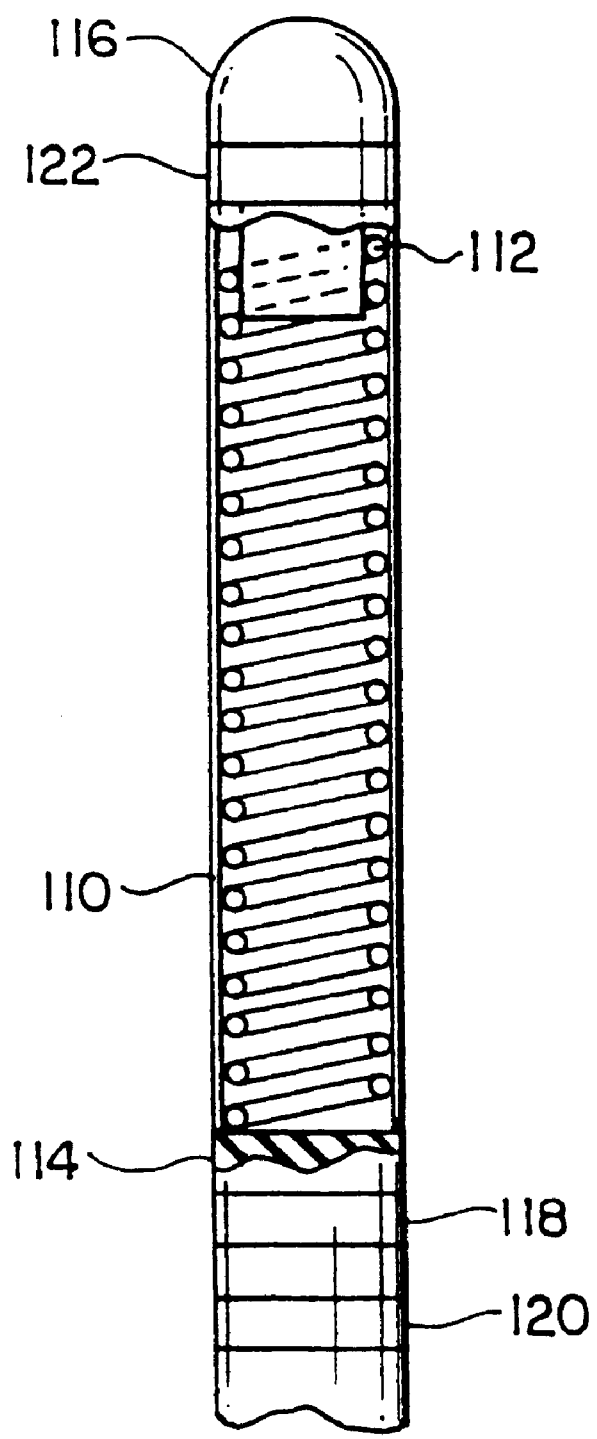
FIG. 24 depicts still another catheter embodiment.

FIG. 24 illustrates still another embodiment of a cryogenic cooling structure that includes a surface or wall 110 including a polymer or elastomer that is thin enough to permit thermal transfer. For example, polyamide, PET, or PTFE having a thickness of a typical angioplasty balloon or less (below 0.006 inches) provides acceptable thermal transfer. However, the thinness of the wall 110 allows it to readily collapse or otherwise deform under vacuum or near vacuum conditions applied to evacuate fluid/gas from the structure. Accordingly, the structure is provided with one or more supporting elements 112 such as a spring. The cooling structure is illustrated in association with a catheter 114 having a closed distal tip 116 and mono or bipolar ECG rings 118, 120, 122. The thermally-transmissive region is approximately 30 mm in length and is effective for thermal transfer over its entire circumference. However, as illustrated in FIG. 11, the thermally-transmissive region can be confined to specific region(s) of the device's circumference.

Figure 25:
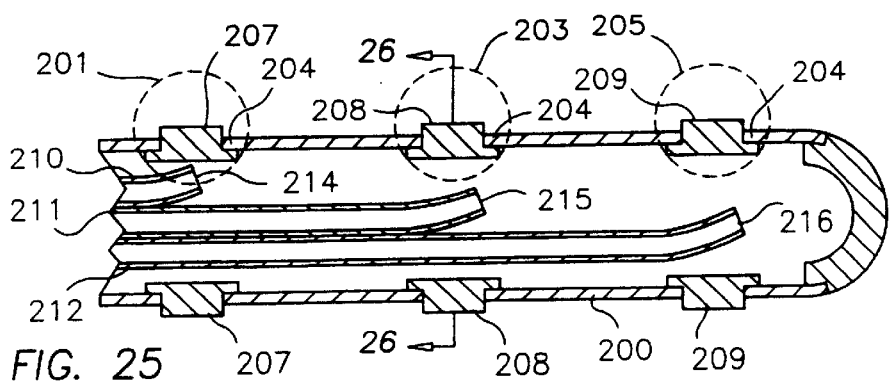
FIG. 25 illustrates yet another embodiment of the catheter.

Referring now to FIG. 25, an embodiment of the catheter is illustrated having three flexible members or injection tubes 210, 211 and 212 disposed within a first or outer flexible member 200. In an exemplary embodiment, the inner flexible members 210, 211 and 212 are arranged in a staggered configuration within the outer flexible member 200. As used herein, term "staggered" may be used to designate both a linearly/axially staggered configuration or alternatively, a rotationally staggered configuration. The flexible members 210, 211 and 212 thus define multiple staggered fluid paths within the outer member 200. In such a configuration, the injection tubes 210, 211 and 212 allow for greater aggregate cooling power as well as the creation of a variety of different cooling/freeze zones 201, 203 and 205 along the length of the outer flexible member 200. In an exemplary embodiment, thermocouples 204 disposed along the outer surface of the outer flexible member 200 may be integrated with an internal feedback loop to provide independent and variable regulation of these freeze zones.

Figures 26, 29, 30:
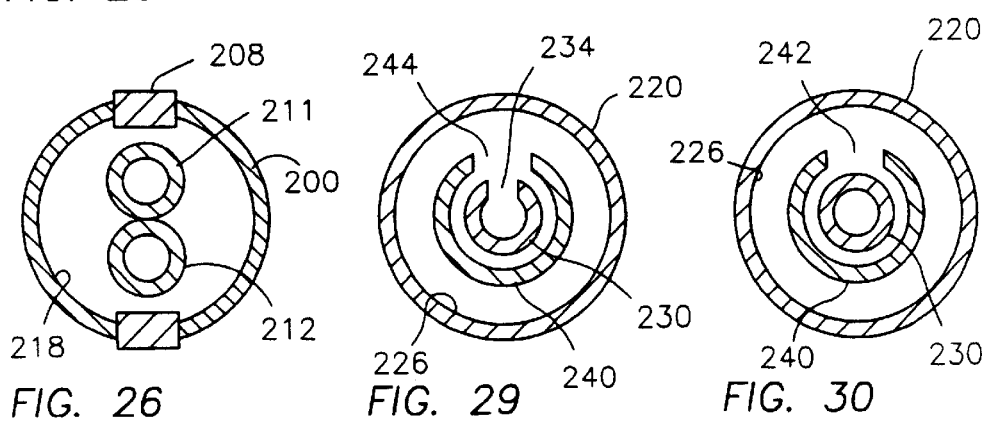
FIG. 26 is a sectional view of the catheter of FIG. 25 taken along line 26—26.
FIG. 29 is a sectional view of the catheter of FIG. 28 taken along line 29—29.
FIG. 30 is a sectional view of the catheter of FIG. 28 taken along line 30—30.

In an exemplary embodiment, the first inner member 210 includes at least one opening 214 positioned proximate an electrode ring member 207. Cryogenic fluid is expelled from the opening 214 and returns to the proximal end of the catheter along a fluid path defined by the inner wall 218 of the outer member 200, as shown in FIG. 26. Similarly, the second inner member 211 includes at least one opening 215 positioned proximate a second electrode ring member 208. Cryogenic fluid is also expelled from the opening 215 and returns to the proximal end of the catheter along the fluid path defined by the inner wall 218 of the outer member 200. Similarly, the third inner member 212 includes at least one opening 216 positioned proximate a third electrode ring member 209.

Alternatively, the catheter can be provided with only two inner members, or four or more inner members, not shown, disposed within the outer member. The inner members would have one or more openings proximate to and/or aligned with the inner face of one or more transmissive elements, as described earlier herein, to achieve different regions of freeze zones across the entire elongate member. Alternatively, all the staggered inner members may be simultaneously provided with cryogenic fluid to create a linear lesion for selected applications. The flow of cooling fluid along the fluid paths through the flexible members can also be alternated in any number of patterns among the multiple inner members to provide a desired cooling pattern such as a discontinuous or a continuous lesion across the entire catheter.

In an exemplary embodiment, a catheter with a plurality of thermally conductive electrode rings would have an underlying injection tube or tubes controlling the release of cryogenic fluid to each electrode. Such a catheter could be placed in the coronary sinus or endocardially along the atrioventricular junction. Once positioned, an electrogram of interest is located using a specific electrode ring on the catheter. Coldmapping may be performed on the selected location to confirm the correctness of the location. Once, confirmed, the area is cryoablated using the same electrode ring. The same embodiments and others described herein are equally suited to other organs besides the heart and/or any body portion that would benefit from the application of thermal energy.

Figure 27:
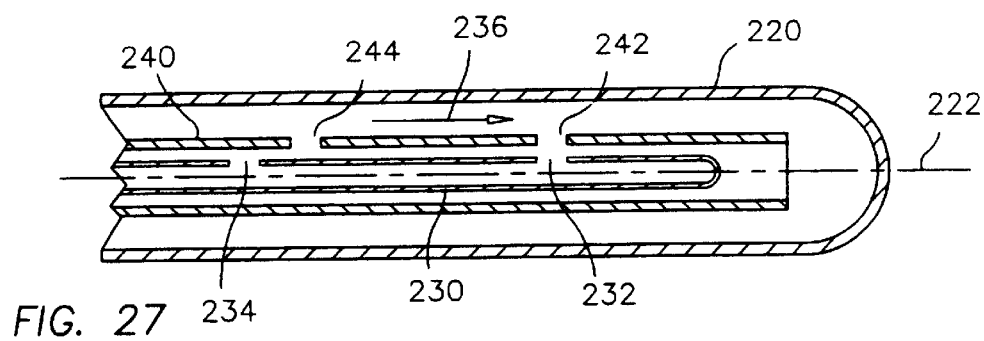
FIG. 27 illustrates yet still another embodiment of the catheter.

Referring now to FIG. 27, an embodiment of the catheter is illustrated having an outer member 220 with a fixed injection tube 230 disposed within a slidable sheath or overtube 240 therein. The injection tube and overtube are shown spaced apart for illustrative purposes only. Preferably, the injection tube is sized so that an outer surface of the injection tube engages an inner surface of the overtube while still allowing one member to slide or rotate relative to the other.

The fixed injection tube 230 has multiple openings 232, 234 formed thereon and the slidable overtube also has multiple openings or ports 242, 244 formed thereon. In one configuration shown in FIG. 27, opening 232 on the injection tube 230 coincides or is aligned with opening 242 on the slidable overtube 240. Thus, any fluid exiting the injection tube 230 from opening 232 is able to escape through opening 242.

Figure 28:
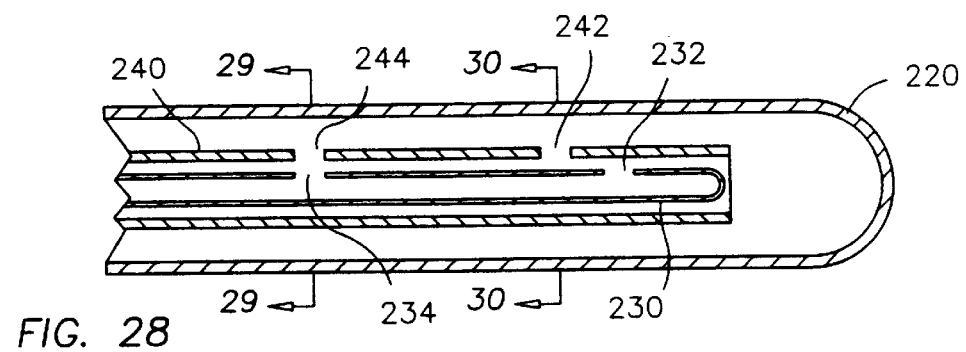
FIG. 28 illustrates the catheter of FIG. 27 in a second configuration.

As the slidable overtube 240 is slid or moved in a first direction as shown by arrow 236 along longitudinal axis 222, opening 232 is covered or blocked by the surface of overtube 240 as now shown in FIG. 28. In a second configuration shown in FIG. 29, opening 234 of injection tube 230 is aligned with opening 244 of overtube 240. In the same configuration, as shown in FIG. 30, opening 242 is not aligned with any opening formed on the surface of injection tube 230. Although only shown in two positions or configurations, the slidable overtube is positionable in any number of positions relative to the fixed injection tube. The overtube may also be used to partially cover the openings on the injection tube to provide for a limited or controlled flow of cryogenic fluid.

Depending on which opening of the injection tube is aligned with the openings formed on the overtube, cryogenic fluid is expelled from the opening and returns to the proximal end of the catheter along a fluid path defined by the inner wall 226 of the outer member 220. The non-aligned opening will not expel fluid since the opening will be blocked. Alternatively, the injection tube and overtube can be provided with three or more openings to achieve multiple cooling/freeze zones along the length of the catheter.

Figure 31:
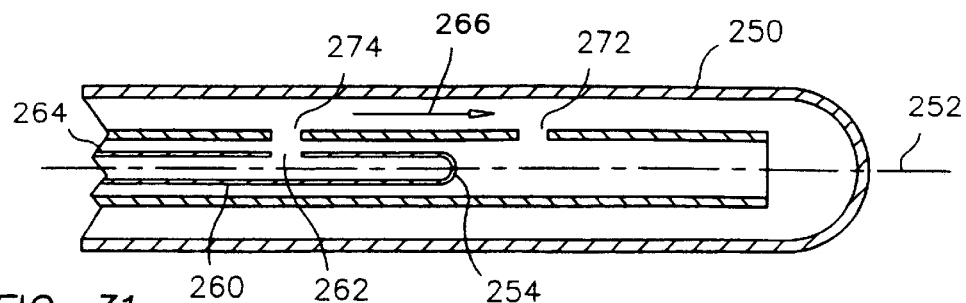
FIG. 31 illustrates yet another embodiment of the catheter.

Referring now to FIG. 31, an embodiment of the catheter is illustrated having a slidable injection tube 260 disposed within a fixed sheath or overtube 270. As shown in FIG. 31, both the injection tube 260 and overtube 270 are disposed within a flexible outer member 250. The slidable injection tube 260 has multiple openings 262, 264 formed thereon which allows for the release of cryogenic fluid. The fixed overtube 270 also has multiple perforations or openings 272, 274 formed thereon which allows for the differential release of fluid as described in more detail below. The injection tube may be further provided with a thermistor 254 disposed proximate the distal end of the tube to provide thermistor feedback. In one embodiment, the openings can be controlled by miniaturized means such as micro or nanovalves.

In a first configuration shown in FIG. 31, opening 262 of the injection tube 260 coincides or is aligned with opening 274 of the fixed overtube 270. As the slidable injection tube 260 is slid or moved in a first direction as shown by arrow 266, opening 262 is then aligned with corresponding opening 272 on the overtube 270 in FIG. 32.

Figure 32:
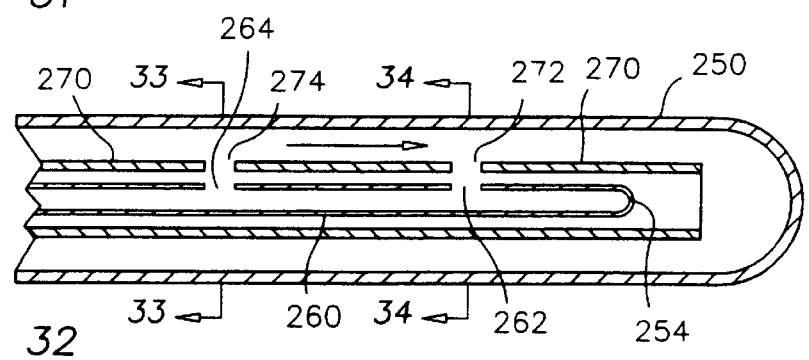
FIG. 32 illustrates the catheter of FIG. 31 in a second configuration.
Figure 33:
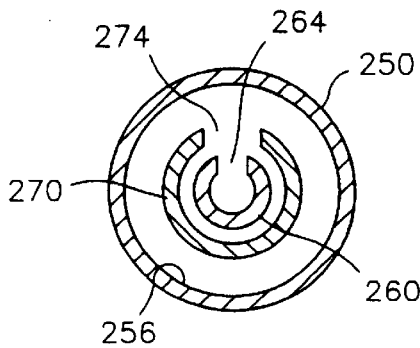
FIG. 33 is a sectional view of the catheter of FIG. 32 taken along line 33—33.
Figure 34:
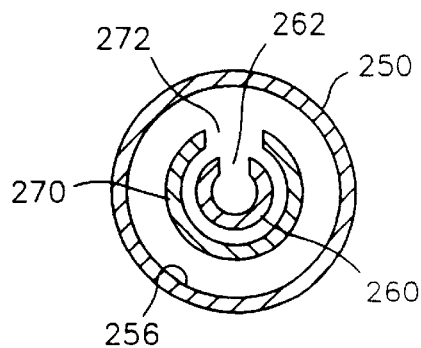
FIG. 34 is a sectional view of the catheter of FIG. 32 taken along line 34—34.

In this second configuration, as shown in FIGS. 32–34, openings 262, 264 of injection tube 260 are aligned with openings 272, 274 of overtube 270. Although only two configurations for the catheter are shown, the injection tube 260 is positionable in any number of locations relative to the fixed overtube 270.

In operation, cryogenic fluid is expelled from the openings and returns to the proximal end of the catheter along a fluid path defined by an inner wall 256 of the outer member 250. Alternatively, the injection tube 260 and overtube 270 can be provided with multiple openings proximate to and/or aligned with the inner face of one or more thermally-transmissive elements as described earlier herein to achieve more uniform cooling across the entire elongate, thermally-transmissive region.

Figure 35:
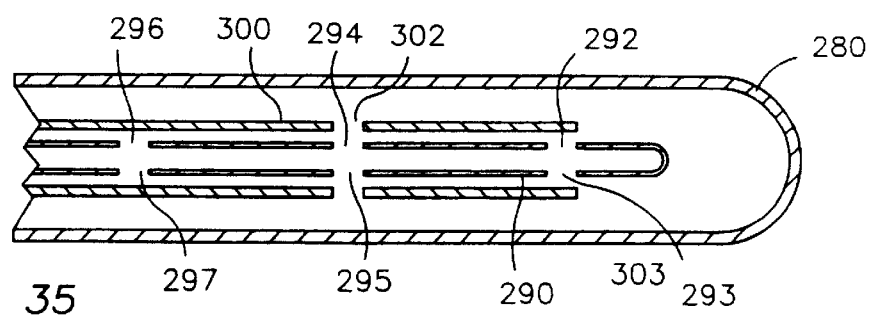
FIG. 35 illustrates yet another embodiment of the catheter.

Referring to FIG. 35, an embodiment of the catheter is illustrated having an outer member 280 with an injection tube 290 with multiple opposed openings 292–297 formed therein. Either the injection tube 290 or the overtube 300 may be slidable in a longitudinal plane to expose and/or cover one or more of the opposed openings on the injection tube 290. For example, as shown in FIG. 35, openings 294, 295 formed on the injection tube 290 are aligned with openings 302, 303 formed on the overtube 230. Furthermore, the injection tube may be positioned in a forwardmost position, not shown, to expose openings on the injection tube proximate the tip of the catheter. In this configuration, the injection tube would provide fluid to cool the area around the tip of the catheter.

In the embodiments described and shown above in FIGS. 32–35, electrode rings as shown in FIG. 25 may be provided along the outer surface of any of the outer members. The electrodes would serve both as electrical conductors and as a thermal transmitter at each location.

Figure 36:
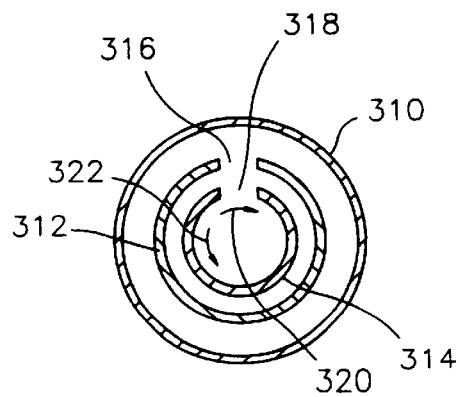
FIG. 36 is a sectional view of yet another embodiment of the catheter.
Figure 37:
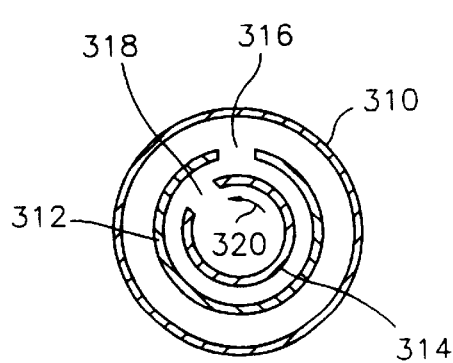
FIG. 37 is a sectional view of the catheter of FIG. 36 after rotation.

Referring to FIGS. 36 and 37, an embodiment of the catheter is illustrated having one or more rotatable members disposed within a flexible outer member 310. In this embodiment, the catheter includes an overtube member 312 and an injection tube member 314, one or both of which are rotatable with respect to one another. In an exemplary embodiment as shown in FIGS. 36 and 37, the injection tube 314 is rotatable relative to the fixed overtube 312. The injection tube 314 may be rotatable in either or both a clockwise and counterclockwise direction as indicated by arrows 320 and 322. As shown in FIG. 36, in a first configuration, opening 316 formed on the overtube 312 aligns with an opening 318 formed on the injection tube 314. As the injection tube 314 is rotated in a counterclockwise direction, the opening 318 on the injection tube 314 is placed out of alignment with the opening 316 formed on overtube 312, as shown in FIG. 37. Alternatively, the injection tube 314 may be fixed in the catheter while the overtube 312 is rotatable. In another embodiment, both the injection tube and overtube may be both be rotatable. In yet a further embodiment, the injection tube and/or the overtube are rotatable and slidable within the outer member.

Figure 40:
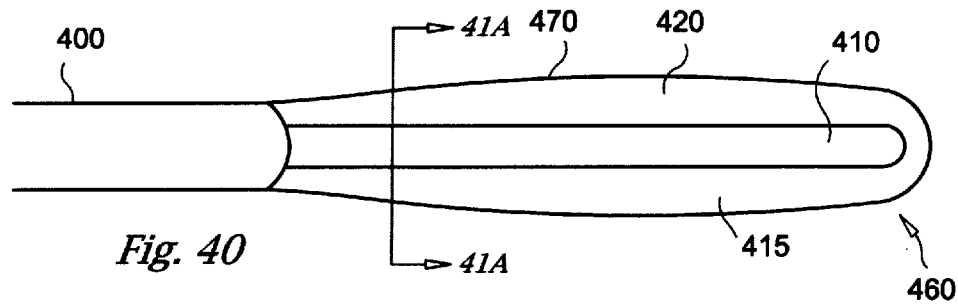
FIG. 40 shows another embodiment of the catheter.
Figures 41A, 41B:
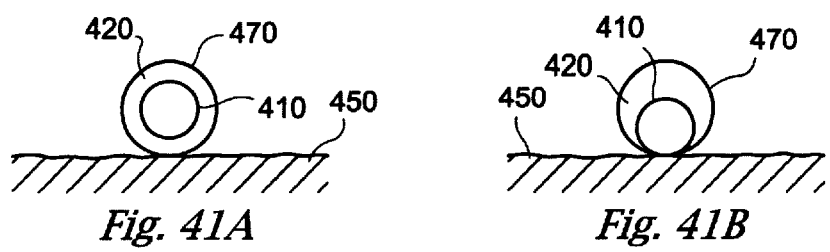
FIG. 41A is a sectional view of the catheter of FIG. 40 taken along Line 40—40.
FIG. 41B is a sectional view of the catheter of FIG. 40 taken along Line 40—40.

Referring now to FIGS. 40, 41A and 41B, a catheter is shown generally as 460 and comprises a pliant outer member 470, a fluid transport member 410 and a catheter body 400. A chamber 420 is formed between the outer member 470 and the fluid transport member 410. The chamber 420 is filled with a bio-compatible fluid 415 that insulates a tissue 450 from the thermal energy present in the fluid transport member 410 when a thermally active fluid is circulated therein.

In operation, the catheter 460 is located within the tissue 450 to be treated as is known in the art using suitable devices such as an electrocardiogram (ECG), fluoroscope or other suitable imaging or locating device and technique. Once the catheter is properly located proximal to the treatment site, the fluid transport member 410 is brought closer to the outer member 470. This is accomplished either by moving the fluid transport member 410 directly or by forcing the pliant outer member 470 against the fluid transport member 410, or even using a combination of the two motions. Various treatments are possible using the above device and method such as, but not limited to, ablations and temporary interruptions of the tissue activity such as cold-mapping of the electrical activity and pathways of cardiac tissue. By varying the relative distance between the fluid transport member 410 and the outer member 470, different temperatures are achievable without varying the thermal content of an energetic fluid. The bio-compatible fluid 415 could be a viscous fluid, gel, thin liquid, or gas. The insulative properties of the fluid 415 are selected to accommodate the desired temperature regime of the medical procedure to be performed.

Figures 42, 43:
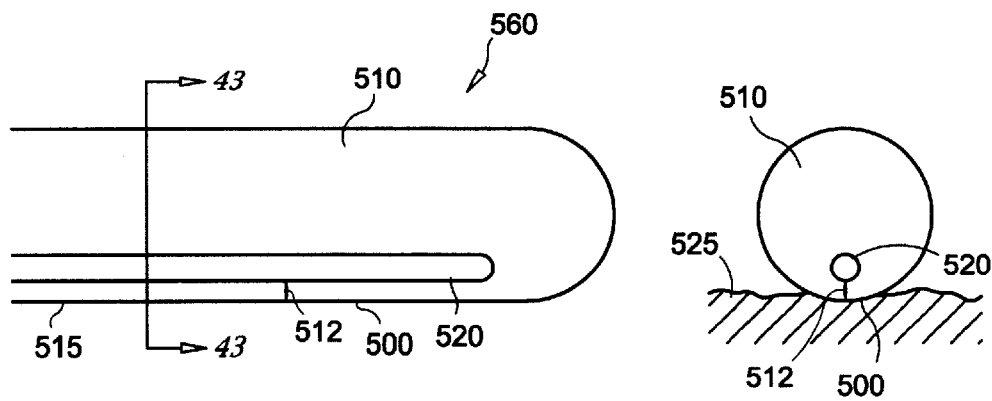
FIG. 42 depicts yet another embodiment of the catheter.
FIG. 43 is a sectional view of the catheter of FIG. 42 taken along Line 42—42.

FIGS. 42 and 43 illustrate another embodiment of the catheter shown generally as 560 and comprises a catheter body 515, a thermally transmissive region 500, a chamber 510, a fluid transport member 520 and a gap 512. The gap 512 is selected to provide a path to conduct the thermal energy contained within the fluid transport member 520 to the thermally transmissive region 500.

In operation, the catheter 560 is located proximal to the selected tissue 525. The fluid transport member 520 is aligned with the tissue 525. The catheter body 515 may be rotated to position the fluid transport member 520. A thermally energetic fluid is circulated within the fluid transport member 520 and the thermal energy contained therein is transferred through the thermally transmissive region 500 to the selected tissue 525.

Although the gap 512 may be fixed, it is within the scope of this embodiment to vary the gap 512 using mechanical means such as a control wire (not shown) or other suitable lumen positioning means as is known in the art. An insulating fluid or material may fill the chamber 510 to provide further protection to non-targeted tissue surrounding the catheter 560. The chamber 510 may also be used to house sensors such as thermocouples, ECG electrodes, etc. (not shown) to further aid in locating and providing data regarding the tissue in contact with the catheter 560.

Figure 44:
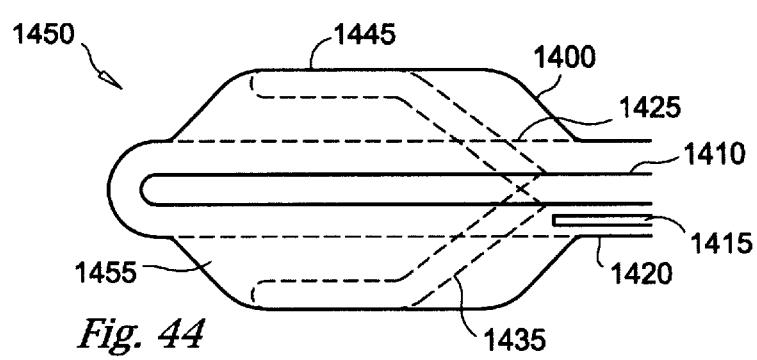
FIG. 44 illustrates another embodiment of the catheter.

Referring to FIG. 44, a catheter 1450 is shown comprising an expandable outer member 1400, a fluid transport member 1410 and a body 1420. The outer member 1400 is expanded and retracted using a chamber inflation member 1415. In the deflated position 1425, the diameter of a thermally transmissive region 1445 is generally close to the diameter of the catheter body 1420. A bio-compatible fluid is injected into a chamber 1455 created between the outer member 1400 and the fluid transport member 1410 using the chamber inflation member 1415. The fluid transport member 1410 is flexible and movable towards the thermally transmissive region 1445. A guide wire (not shown) or other suitable method of moving the fluid transport member 1410 such as using a memory material to deform the fluid transport member 1410 to a position 1435 is used to transfer the thermal energy contained in the fluid transport member 1410 to the thermally transmissive region 1445 which is in contact with the selected tissue (not shown). After treatment, the fluid transport member 1410 is moved back to a neutral position and the chamber 1455 is deflated by removing fluid from the chamber 1455 using the chamber inflation member 1415.

Figure 46:
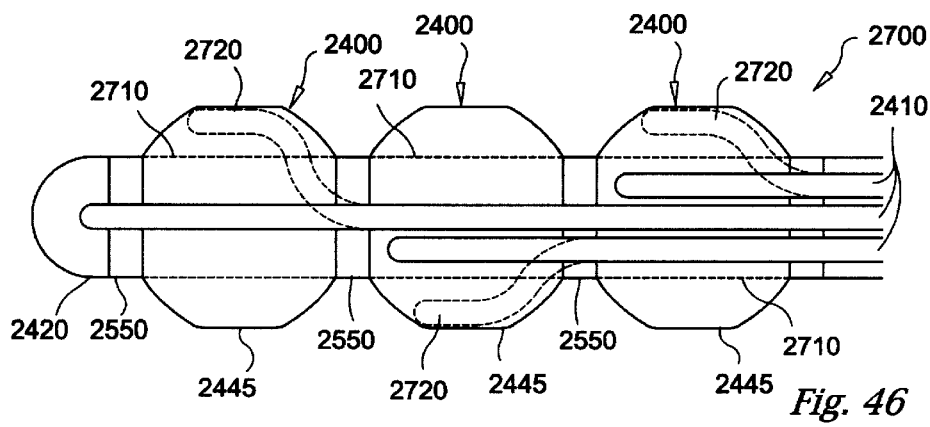
FIG. 46 depicts another embodiment of the catheter.

Referring now to FIG. 46, a multiple treatment zone catheter 2700 is shown comprising a plurality of thermally transmissive regions 2400, a plurality of outer members 2445, a body 2420 and a plurality of fluid transport members 2410. Additionally, sensors 2550 are utilized to help locate the catheter 2700 and to provide data such as the temperature of the catheter 2700 or tissue contacting the catheter 2700. Each of the outer members 2445 are inflatable between an expanded position and a deflated position 2710. Each of fluid transport members 2410 are movable between a neutral position and a deflected position 2720. When the fluid transport member 2410 is positioned adjacent to the thermally transmissive region 2400, energy is transferred to the tissue in proximity to the region 2400. In one embodiment, the multiple treatment zone catheter 2700 is flexible to enable the thermally transmissive regions to be advantageously positioned within the selected tissue (as shown in FIGS. 47 and 48).

Figure 47:
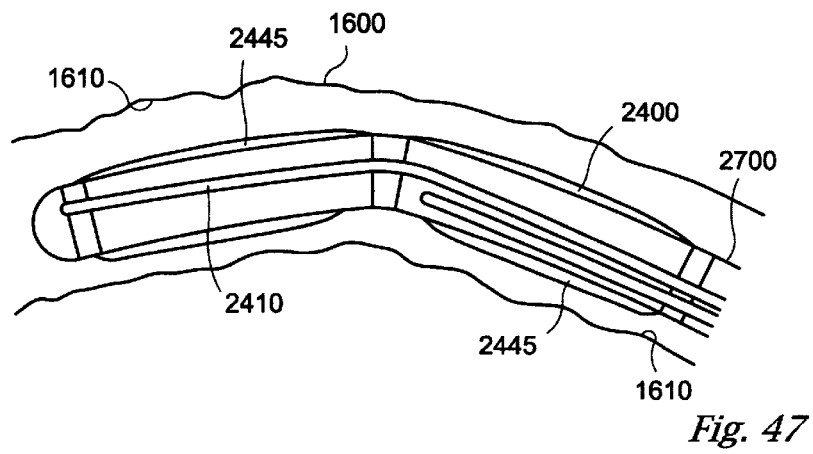
FIG. 47 illustrates insertion of an embodiment of the catheter within tissue.
Figure 48:
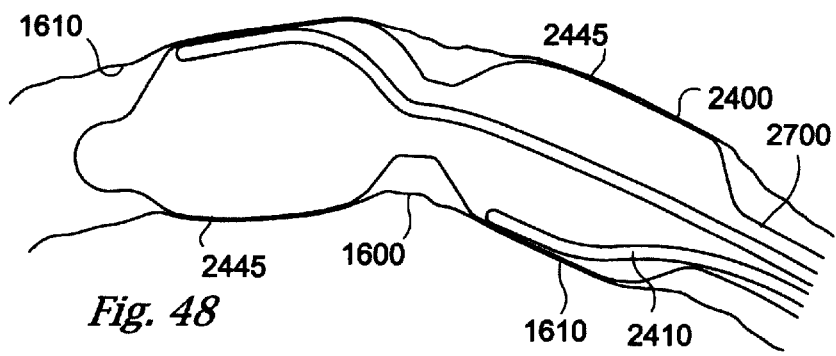
FIG. 48 illustrates inflation of the catheter of FIG. 47 within tissue.

In operation, FIGS. 47 and 48 illustrate the method of using the multiple treatment zone catheter 2700 within the tissue 1600. Treatment sites 1610 are selected and the catheter 2700 is positioned to line up the thermally transmissive regions 2400 with the selected sites 1610. Often, the treatment sites 1610 are not smooth (as shown in FIG. 47). Once the outer members 2445 are expanded against the sites 1610, the sites 1610 are smoothed (as shown in FIG. 48) and made more amenable to treatment. Each fluid transport member 2410 is moved into position adjacent to the thermally transmissive regions 2400. A thermally energetic fluid is then circulated within the fluid transport members 2410 for an amount of time selected to perform a medical procedure such as ablation, etc. The fluid transport members 2410 may be repositioned without moving the rest of the catheter 2700 to perform further treatments. The outer members 2445 are then deflated and the catheter 2700 is repositioned or removed depending on the procedure.

Figure 49:
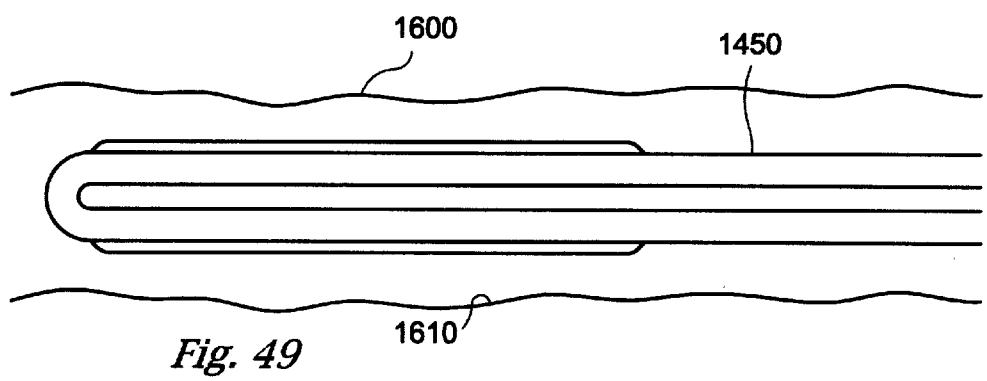
FIG. 49 shows yet another embodiment of the catheter within tissue.
Figure 50:
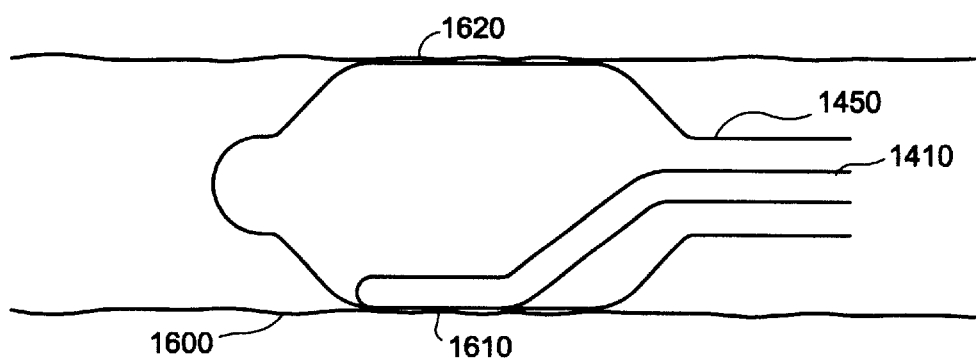
FIG. 50 depicts the catheter of FIG. 49 after inflation within tissue.

Now referring to FIGS. 49 and 50, a catheter 1450 having a single treatment region is shown in operation. Again, in a similar manner as discussed above, the catheter 1450 is inserted in the tissue 1600. The uneven surface of the tissue 1600 is smoothed and stretched by expanding the outer member 1620 against the tissue 1600. The fluid transport member 1410 is moved towards the treatment site 1610 and thermal energy is transferred to the tissue 1600 proximal to the treatment site 1610. As discussed above with respect to the multiple treatment zone catheter 2700, the catheter 1450 is removed or repositioned or the fluid transport member 1410 is repositioned for further treatments.

Figure 51:
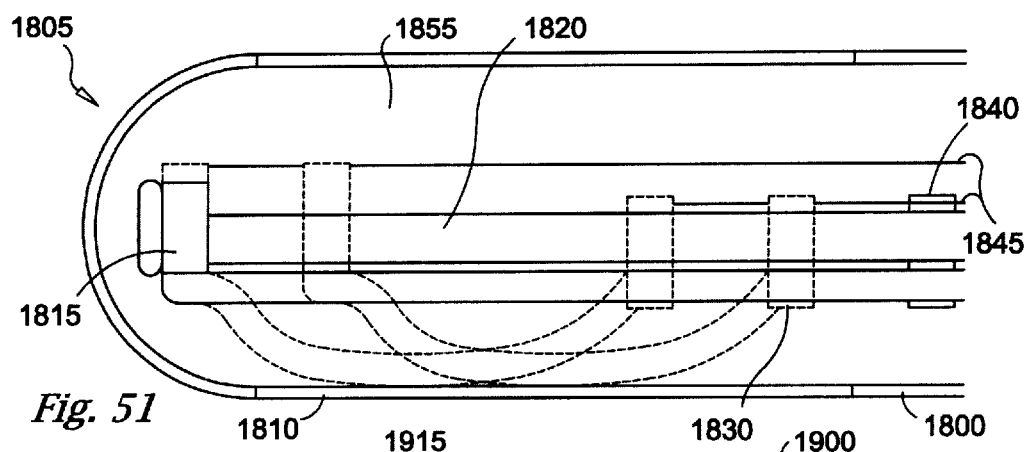
FIG. 51 illustrates another embodiment of the catheter.

Referring now to FIG. 51, an embodiment of a sliding treatment catheter 1805 is shown as comprising a body 1800, a thermally transmissive region 1810, a fluid transport member 1830, a support slide 1820, a support cap 1815, and a sliding contact 1840. The fluid transport member 1830 is deformable and moves towards or away from the thermally transmission region 1810 when the sliding contact 1840 is moved. A wire 1845 is used to move sliding contact 1840 (or any other means of applying a linear force to the sliding contact 1840). A chamber 1855 may be formed between the thermally transmissive region 1810 and the fluid transport member 1830. The chamber 1855 is filled with an insulative bio-compatible fluid to isolate non-selected tissue from the thermal energy contained within the fluid transport member 1830. Sensors such as thermocouples and ECG electrodes (not shown) may be located within the chamber or on the surface of the thermally transmissive region 1810 or body 1800 to provide information to an operator.

In another embodiment, the catheter 1805 may include a rotatable fluid transport member 1830. In the rotatable embodiment, the sliding contact 1840 is also able to rotate around the support slide either in tandem with or independently of the support cap 1815. This embodiment allows treatment to occur anywhere within the circumference of the thermally transmissive region 1810 without repositioning the entire catheter 1805. Additionally, linear treatment patterns are selected by rotating both the support cap 1815 and the sliding contact 1830 in tandem, and curved treatment patterns are selected by holding either the sliding contact 1840 or the support cap 1815 stationary while rotating the other or by counter rotating the sliding contact 1840 and the support cap 1815.

Figure 52:
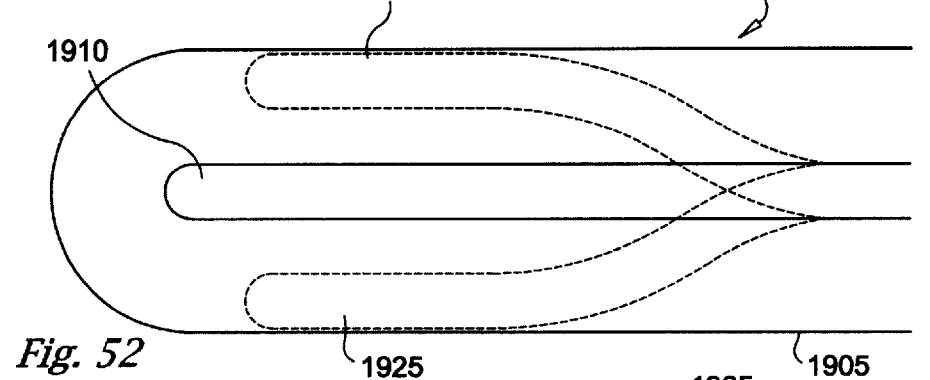
FIG. 52 shows yet another embodiment of the catheter.

Referring now to FIG. 52, a catheter 1900 is illustrated as comprising a body 1905, a thermally transmissive region 1915 and a movable fluid transport member 1910. This embodiment is similar to the catheter shown in FIG. 44, however, the catheter 1900 utilizes a constant diameter thermally transmissive region 1915 instead of an inflatable region as shown in FIG. 44. Because the thermally transmissive region 1915 does not inflate, the thermally transmissive region 1915 must be placed in proximity to the selected tissue to begin the process. After positioning the thermally transmissive region 1915 in proximity to the selected tissue, the fluid transport member 1910 is moved proximally to the thermally transmissive region 1915 and thermal energy is applied to the target tissue (not shown) to perform the treatment.

Figure 53:
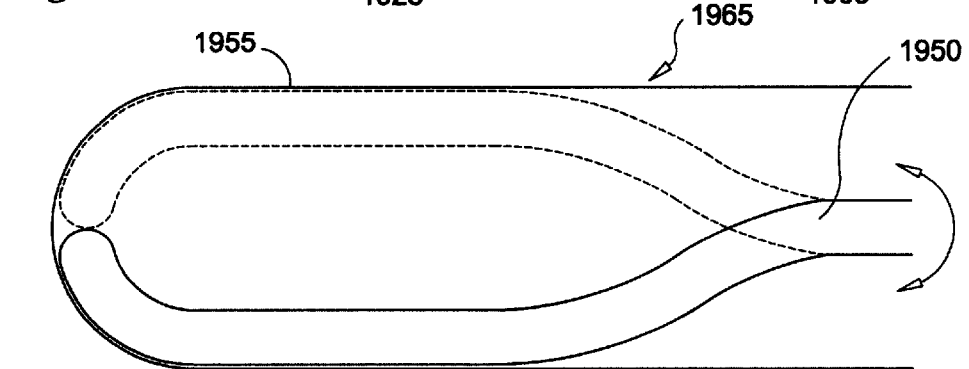
FIG. 53 depicts another embodiment of the catheter.

Another embodiment of a catheter, shown generally as 1965 in FIG. 53, comprises a body 1960, a thermally transmissive region 1955 and a rotatable fluid member 1950.

Once the thermally transmissive region 1955 is proximally positioned in a selected tissue (not shown), the fluid transport member 1950 is rotated to align the portion of fluid transport member 1950 adjacent to the interior surface of the thermally transmissive region 1955 with the selected treatment site (not shown). A thermally active fluid is circulated within the fluid transport member 1950 for a medically effective period of time based on the desired procedure. After the required transfer of thermal energy to the selected site, the fluid transport member 1950 may be rotated to a new position and the process repeated or the catheter 1965 may be removed.

Figure 54:
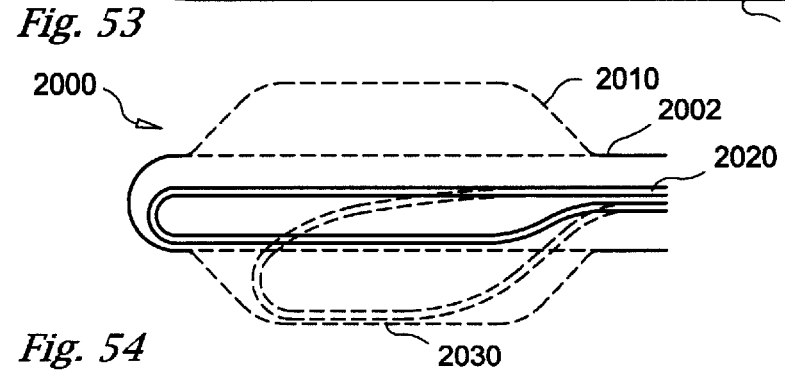
FIG. 54 illustrates another embodiment of the catheter.

A further embodiment is illustrated in FIG. 54 showing a catheter 2000 as comprising a body 2002, an outer member 2010, a movable fluid transport member 2020 and a thermally transmissive region 2030. The fluid transport member 2020 is flexible and is placed proximal to the outer member 2010 when the outer member 2010 is inflated. In one embodiment, the fluid transport member 2020 is also rotatable to provide treatment zones all along the thermally transmission region 2010 without repositioning the entire catheter 2000 or rotating the body 2002.

Figure 38:
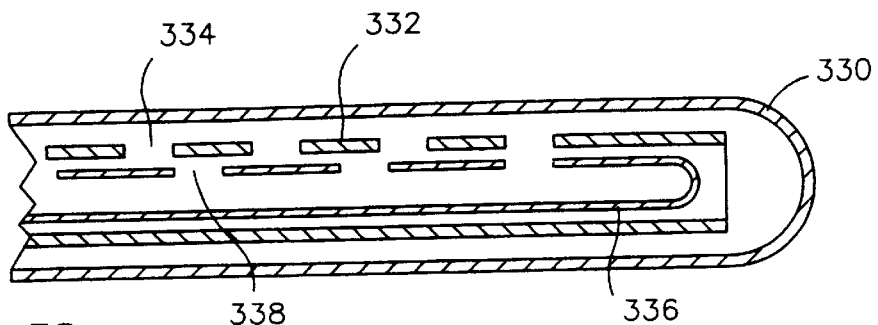
FIG. 38 illustrates yet another embodiment of the catheter.
Figure 39:
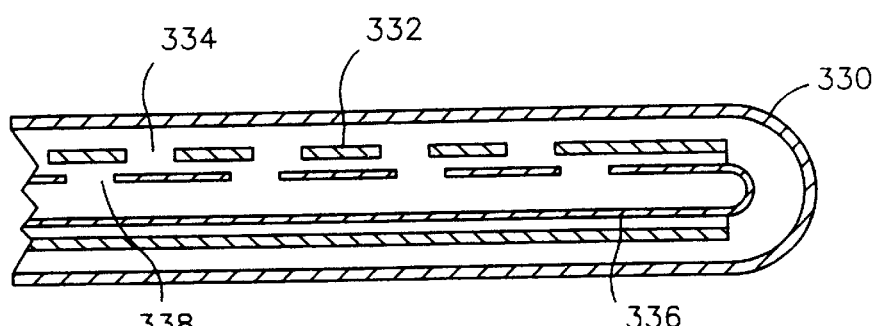
FIG. 39 illustrates the catheter of FIG. 38 in a second configuration.

In the embodiments shown and described above, the slidable and rotatable inner and outer tubes may have openings so arranged as to allow the fluid releasing openings to be in a variety of open and closed configurations with a minimum of relational movement between the tubes. For example, as shown in FIG. 38, an outer member 330 has disposed therein one slidably disposed inner tube 336 which has openings 338 formed thereon in a constant sequence, and a matching slidably disposed outer tube 332 which has openings 334 formed thereon in a constant sequence of slightly different length or intervals. In this configuration, as shown in FIG. 39, small linear relational movements bring the openings on the outer tube 332 and the inner tube 336 into an overlapping configuration.

In addition, the openings as shown and described herein may be so shaped as to allow additional control of fluid release. For example, an outer hole could be tear-shaped and match up with an inner opening that is tear-shaped rotationally aligned 180° oppositely not shown. As the two narrow ends begin to overlap with slidable motion, a tiny aperture is created. With further slidable motion in the same direction, larger areas of the two openings overlap and larger volumes of cryogenic fluid can be released.

Figure 45:
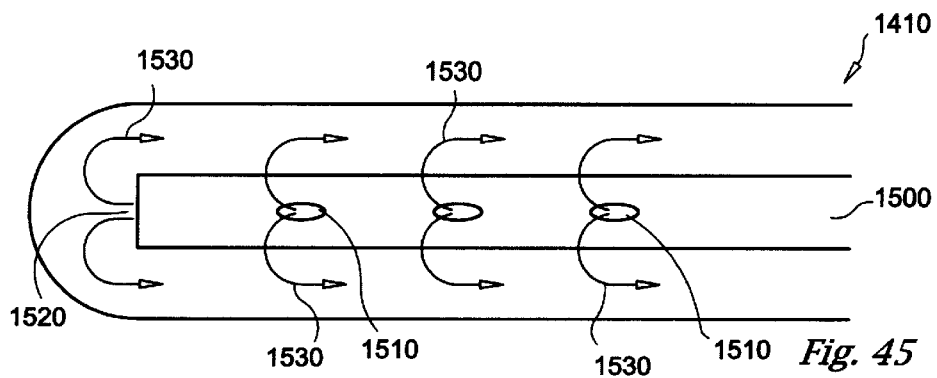
FIG. 45 shows the detail of a fluid transport member according to an embodiment of the invention.

A typical fluid transport member 1500 is illustrated in FIG. 45. As shown and discussed with reference to FIGS. 25–39, the fluid transport member, shown generally as 1410, allows an energetic fluid 1530 to be circulated within an outer wall 1502. A conduit 1500 injects the fluid 1530 into the space formed between the wall 1502 and the conduit 1500. A series of holes 1510 or a conduit end opening 1520 or a combination of both may be used to direct the fluid 1530 within the fluid transport member 1410. The conduit may be flexible or rigid depending on the required use. The wall 1502 is also flexible or rigid to complement the conduit 1500 and required use. Other embodiments of the fluid transport member 1410 include a solid thermally transmissive conduit 1500 where the energetic fluid transfer of energy takes place before reaching the end of the fluid transport member 1410. In an alternative embodiment, the entire end of the transport member 1410 is a thermally transmissive solid which is thermally activated prior to reaching the end and the energy is transmitted along the fluid transport member 1410 without actually circulating the fluid 1530 at the end therein.

A variety of modifications and variations of the present invention are possible in light of the above teachings. Specifically, although many embodiments are illustrated being slender and flexible, other embodiments may be thick and rigid, and introduced into the body directly through incisions or through structures such as trocars. The opening and closing of the catheter openings may also be controlled by using nanotechnology and miniaturized valving. Furthermore, although some of the illustrated devices are particularly well suited for cardiac procedures, the same embodiments and others are equally suited to other organs and/or any body portion that would benefit from the application of thermal energy. For example, the illustrated devices may be used for treating arteries for restenosis or portions of the GI tract to stop bleeding or portions of the GU tract to treat spasm, inflammation, obstruction or malignancy. Thus, the devices as shown are not to be limited to catheters but should be viewed more broadly as cryogenic structures or portions thereof. It is therefore understood that, within the scope of the appended claims, the present invention may be practiced otherwise than as specifically described hereinabove. All references cited herein are expressly incorporated by reference in their entirety.

What is claimed is:

1. A medical device having a body comprising:
   a fluid transport member disposed within the body and configured to circulate fluid therein;
   an outer member substantially surrounding the fluid transport member;
   the body having a portion defining a chamber disposed between the outer member and the fluid transport member; and
   means to vary a relative distance between the outer member and the fluid transport member.

2. The medical device according to claim 1, wherein the outer member includes a flexible portion.

3. The medical device according to claim 2, further comprising means for expanding the flexible portion to make contact with a selected tissue region.

4. The medical device according to claim 1, wherein the means to vary the relative distance between the outer member and the fluid transport member includes a moveable fluid transport member.

5. The medical device according to claim 1, wherein the outer member is deformable.

6. The medical device according to claim 5, wherein the means to vary the relative distance between the outer member and the fluid transport member compresses the deformable outer member.

7. The medical device according to claim 3, wherein the means for expanding the flexible portion is an inflation tube for injecting an inflation fluid into the chamber.

8. The medical device according to claim 3, wherein the fluid transport member includes means for circulating an energetic fluid therein.

9. The medical device according to claim 1, further comprising means for moving the fluid transport member.

10. The medical device according to claim 5, further comprising means for deforming the outer member.

11. The medical device according to claim 1, wherein the energetic fluid is a cryogenic fluid.

12. A medical device comprising:
    a thermally transmissive region; and
    an axially off-set fluid path thermally coupled to at least a portion of the thermally transmissive region, wherein the axially off-set fluid path is adjacent to an inner surface of the thermally transmissive region, wherein the axially off-set fluid path includes means for circulating an energetic fluid therein.

13. The medical device according to claim 12, wherein the energetic fluid is a cryogenic fluid.

14. A medical device having a body comprising:
   a thermally transmissive region disposed on the surface of the body;
   a rotatable fluid transport member thermally coupled to the thermally transmissive region; and
   the rotatable fluid transport member having at least one segment positionable proximal to an inner surface of the thermally transmissive region.

15. The medical device according to claim 14, wherein the rotatable fluid transport member is flexible.

16. The medical device according to claim 15, further comprising:
   a support slide disposed within the body and proximal to the thermally transmissive region;
   a sliding contact moveably coupled to the support slide; and
   the rotatable fluid transport member being coupled to the sliding contact, wherein when the sliding contact is moved, the rotatable fluid transport member is deformed.

17. The medical device according to claim 16, further comprising means for sliding and rotating the deformed rotatable fluid transport member along the support slide.

18. The medical device according to claim 14, wherein the rotatable fluid transport member includes means for circulating an energetic fluid therein.

19. A medical device having a body comprising:
   a thermally transmissive region disposed on the surface of the body;
   a support slide disposed within the body and proximal to the thermally transmissive region; and
   a flexible fluid transport member slideably mounted to the support slide.

20. The medical device according to claim 19, further comprising means for sliding and rotating the flexible fluid transport member along the support slide.

21. The medical device of claim 19 wherein, the flexible fluid transport member includes means for circulating an energetic fluid therein.

22. The medical device of claim 21 wherein, the energetic fluid is a cryogenic fluid.

23. A method of treating a selected portion of tissue comprising:
   providing an appropriate medical device having a fluid transport path and a thermally transmissive region disposed therein;
   positioning the medical device within the selected portion of tissue;
   inflating a flexible member substantially surrounding the thermally transmissive region;
   moving the fluid transport path to a selected portion of the flexible member; and
   circulating a thermally active fluid within the fluid transport path to deliver a medically effective amount of thermal energy to the selected portion of tissue.

24. The method of claim 23 wherein, the medically effective amount of thermal energy is selected to be an amount effective for ablating the selected portion of tissue.

25. The method of claim 23 wherein, the medically effective amount of thermal energy is selected to be an amount effective for temporarily disrupting a biological activity of the selected portion of tissue.

26. The method of claim 23 further comprising:
   moving the fluid transport path to a second selected portion of tissue; and
   circulating the thermally active fluid within the fluid transport path to deliver a second medically effective amount of thermal energy to the second selected portion of tissue.

27. A method of delivering a medically efficacious amount of energy to a selected tissue using a medical device having a thermally transmissive region, an expandable membrane substantially surrounding the thermally transmissive region and a thermal fluid path thermally coupled to the thermally transmissive region comprising:
   positioning at least a portion of the thermally transmissive region adjacent to the selected tissue;
   activating the expandable membrane to compress the selected tissue;
   moving the thermal fluid path to a position proximal to an inner surface of the expandable membrane;
   circulating a thermally active fluid within the thermal fluid path; and
   transferring a therapeutic amount of energy to the selected tissue.

28. A method of treating a tissue comprising:
   providing a medical device having a thermally transmissive region and an axially off-center fluid path thermally coupled to the thermally transmissive region;
   positioning at least a portion of the thermally transmissive region proximal to the tissue to be treated;
   positioning the axially off-center fluid path closest to the portion of the thermally transmissive region proximal to the tissue to be treated; and
   circulating an energetic fluid within the axially off-center fluid path.

29. A method of treating a selected tissue comprising:
   providing a medical device having a thermally transmissive region, an expandable member substantially surrounding the thermally transmissive region and a moveable fluid path thermally coupled to the thermally transmissive region;
   expanding the expandable member against the selected tissue;
   moving the moveable fluid path in a direction towards the selected tissue; and
   circulating an energetic fluid within the moveable fluid path to deliver a medically effective amount of thermal energy to the selected tissue.

30. A method of treating a selected tissue comprising:
   providing a medical device having a body, a fluid transport member disposed within the body, an outer member substantially surrounding the fluid transport member, the body having a portion defining a chamber disposed between the outer member and the fluid transport member; and means to vary a relative distance between the outer member and the fluid transport member;
   positioning the medical device to contact the selected tissue;
   expanding the outer member by injecting a biocompatible fluid into the chamber;
   decreasing the relative distance between the fluid transport member and the outer member until a selected distance is reached; and
   injecting a thermally active fluid into the fluid transport member for a medically effective period of time.

31. The method of claim 30 wherein, the fluid transport member moves towards the selected tissue when decreasing the relative distance between the fluid transport member and the outer member until the selected distance is reached.

32. The method of claim 30 wherein, a portion of the outer member disposed between the fluid transport path and the selected tissue is compressed thereby decreasing the relative distance between the fluid transport member and the outer member until the selected distance is reached.

33. A method of treating a selected tissue comprising:

providing a medical device having a body, a thermally transmissive region disposed on the surface of the body, a fluid transport member thermally coupled to the thermally transmissive region, the fluid transport member having at least one segment positionable proximal to an inner surface of the thermally transmissive region, and means for moving fluid transport member;

positioning the medical device to contact the selected tissue;

injecting a thermally active fluid within the fluid transport member; and moving the fluid transport member in a selected pattern to perform a desired treatment on the selected tissue.

\* \* \* \* \*